(12) United States Patent
Sheu et al.

(10) Patent No.: US 8,530,513 B1
(45) Date of Patent: Sep. 10, 2013

(54) PHARMACEUTICAL USES OF DITERPENE EXCAVATOLIDE B FROM A CORAL OR AN ANALOGUE THEREOF

(71) Applicant: National Sun Yat-Sen University, Kaohsiung (TW)

(72) Inventors: Jyh-Horng Sheu, Kaohsiung (TW); Ning-Sun Yang, Kaohsiung (TW); Wen-Chi Wei, Kaohsiung (TW); Chiung-Yao Huang, Kaohsiung (TW)

(73) Assignee: National Sun Yat-Sen University, Kaohsiung (TW)

( * ) Notice: Subject to any disclaimer, the term of this patent is extended or adjusted under 35 U.S.C. 154(b) by 0 days.

(21) Appl. No.: 13/725,491

(22) Filed: Dec. 21, 2012

(30) Foreign Application Priority Data

Jun. 21, 2012 (TW) .............................. 101122271 A

(51) Int. Cl.
*A61K 31/35* (2006.01)

(52) U.S. Cl.
USPC ........................................................ 514/455

(58) Field of Classification Search
USPC ........................................................ 514/455
See application file for complete search history.

(56) References Cited

PUBLICATIONS

Wen-Chi Wei, et al., "Topical application of marine briarane-type diterpenes effectively inhibits 12-tetradecanoylphorbol-13-acetate-induced inflammation and dermatitis in murine skin", Journal of Biomedical Science 2011, 18:94.
Libby, "Inflammation and Cardiovascular disease Mechanisms", Am J Clin Nutr, 2006, 83:456S-460S.
Ross, "Atherosclerosis—An Inflammatory Disease", N Engl J Med, 1999, 340: 115-126.
Lucas et al., "Atherosclerosis: Role of Chemokines and Macorphages", 2001, Exp Rev Mol Med 3:1-18.
Gordon, "The Macrophage", Bioassays, 1995, 17:977-986.
Cipollone, "COX-2 and Prostaglandins in Atherosclerosis", Lupus, 2005, 14:756-759.
Boyle, "Macrophage Activation in Atherosclerosis: Pathogenesis and Parmacology of Plaque Rupture", Curr Vasc Pharmacol, 2005, 3:63-68.
Baker et al, "Cyclooxygenase—Is widely expressed in atherosclerotic lesions affecting native and transplanted human coronary arteries and colocalizes with inducible nitric oxide synthase and nitrotyrosine particularly in macrophages", Arterioscler Thromb Vasc Biol, 1999, 19:646-655.
Buttery et al, "Inducible Nitric Oxide synthase is present within human atherosclerotic lesions and promotes the formation and activity of peroxynitrite", Lab Invest, 1996, 75:77-85.
Burleigh et al, "Cyclooxygenase-2 promotes early atherosclerotic lesion formation in LDL receptor-deficient mice," Circulation, 2002, 105:1816-23.
Hayashi et al, "Selective iNOS inhibitor, ONO1714 successfully retards the development of high-cholesterol diet induced atherosclerosis by novel mechanism", Atherosclerosis, 2006, 187:316-324.
Turini et al., "Cyclooxygenase-2: a therapeutic target," Annual Rev Med, 2002, 53:35-57.
Handy et al, "a comparison of the effects of L-NAME, 7-NI, and L-NIL on carrageenan-induced hindpaw oedema nad NOS activity", Br J Pharmacol, 1998, 123:1119-1126.
Osborne et al, "effects of intrathecal administration of nitric oxide sythase inhibitors on carrageenan-induced thermal hyperalgesia", Br J Pharmacol, 1999, 126:1840-1846.
Moalem and Tracey, "Immuneand inflammatory mechanisms in neuropathic pain", Brain Res Rev, 2006, 51:240-264.
Cuzzocrea et al, Effects of combination M40403 and DexamethasoneTherapy on joint disease in a rat model of collagen-induced arthritis, Arthritis Rheum., 2005, 52:1929-40.
Toriyabe et al, Contribution of interaction between nitric oxide and cyclooxygenases to the production of prostaglandins in carrageenan-induced infammation, Anesthesiology, 2004, 101, 983-990.
Lopez-Vales et al, "Effects of COX-2 and iNOS inhibitors alone or in combination with olfactory ensheathing cell grafts after spinal cord injury", Spine., 2006, 31:1100-6.
Kupper TS and Fuhlbrigge RC, "Immune surveillance in the skin: mechanisms and clinical consequences", Nature reviews Immunology, 2004, 4:211-222.
Nestle FO et al., "Skin immune sentinels in health and disease", Nature reviews Immunology, 2009, 9:679-691.
Jermy A. "From the editors", Nature Reviews Immunology, 2010, 10:1.
Nagaoka I, Hirota S., "Increased expression of matrix metalloproteinase-9 in neutrophils in glycogen-induced peritoneal inflammation of guinea pigs", Inflamm Res, 2000, 49:55-62.
De Vry CG, et al., "Topical Application of a Novel Immunomodulatory Peptide, RDP58, Reduces Skin Inflammation in the Phorbol Ester-Induced Dermatitis Model", J Invest Dermatol, 2005, 125:473-481.
Cumberbatch M, Dearman RJ, Kimber I. Immunology 1996, 87:513-518.
Stanifortha V, Huang WC, Aravindaram K, Yang NS. The Journal of Nutritional Biochemistry, 2012, 23:443-451.
Nair HB, Sung B, Yadav VR, Kannappan R, Chaturvedi MM, Aggarwal BB. Biochem Pharmacol 2010, 80:1833-1843.
Wang CY, Staniforth V, Chiao MT, Hou CC, Wu HM, Yeh KC, Chen CH, Hwang PI, Wen TN, Shyur LF, Yang NS. BMC Genomics 2008, 9:479.
Staniforth V, et al, "Constitutive and inducible expression of interleukin-6 by Langerhans cells and lymph node dendritic cells", J Biol Chem, 2004, 279:5877-5885.

(Continued)

*Primary Examiner* — Raymond Henley, III
(74) *Attorney, Agent, or Firm* — WPAT, P.C.; Anthony King

(57) ABSTRACT

The invention relates to use of a diterpene from a coral, excavatolide B, or an analogue thereof for treating a disease associated with inducible nitric oxide synthase, cyclooxygenase-2 and/or matrix metalloproteinase. The invention also relates to use of a diterpene from a coral, excavatolide B, and an analogue thereof for treating a disease associated with TNF-α and/or IL-6 over-expression.

20 Claims, 12 Drawing Sheets

(56) References Cited

PUBLICATIONS

Staniforth V, et al., "Caffeic acid suppresses UVB radiation-induced expression of interleukin-10 and activation of mitogen-activated protein kinases in mouse", Carcinogenesis, 2006, 27:1803-1811.

Marris E., "Drugs from the deep", Nature, 2006, 443:904-905.

Blunt JW, et al., "Marine natural products", Nat Prod Rep, 2005, 22:15-61.

Sheu JH, et al., "Novel Cytotoxic Diterpenes, Excavatolides A-E, Isolated from the Formosan Gorgonian Briareum excavatum", J Nat Prod, 1998, 61:602-608.

Sheu JH, et al., "Excavatolides U-Z, New Briarane Diterpenes from the Gorgonian Briareum excavatum", J Nat Prod, 1999, 62:1415-1420.

Misko et al, "Mediation of inflammation by encephalitogenic cells: interferon y induction of nitric oxide synthase and cyclooxygenase 2", J Neuroimmunol., 1995, 61:195-204.

Stamenkovic I, "Extracellular matrix remodelling: the role of matrix metalloproteinases", J Pathol, 2003, 200:448-464.

Shakarjian MP et al., "Preferential expression of matrix metalloproteinase-9 in mouse skin after sulfur mustard exposure", J Appl Toxicol, 2006, 26:239-246.

Rao TS et al., "Comparative Evaluation of Arachidonic Acid (AA)- and Tetradecanoylphorbol Acetate (TPA)-Induced Dermal Inflammation", Inflammation, 1993, 17:723-741.

Thurston G et al., "Leakage-Resistant Blood Vessels in Mice Transgenically Overexpressing Angiopoietin-1", Science 1999, 286:2511-2514.

Yin sY et al., "Stimulatory effect of *Echinacea purpurea* extract on the trafficking activity of mouse dendritic cells: revealed by genomic and proteomic analyses", BMC genomics, 2010, 11:612.

Vane JR et al., "Inducible isoforms of cyclooxygenase and nitric-oxide synthase in inflammation", Proc Natl Acad Sci U S A, 1994, 91:2046-2050.

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: sense primer

<400> SEQUENCE: 1
ctagtgagag actctacacg gag                                    23

<210> SEQ ID NO 2

```
<211> LENGTH: 23
<212> TYPE: DNA
<213> ORGANISM: Artificial Sequence
<220> FEATURE:
<223> OTHER INFORMATION: anti-sense primer

<400> SEQUENCE: 2
gagccacgac catacagata ctg                                            23

<210> SEQ ID NO 3
<211> LENGTH: 27
<212> TYPE: DNA
<213> ORGANISM: Artificial Sequence
<220> FEATURE:
<223> OTHER INFORMATION: sense primer

<400> SEQUENCE: 3
catcactgcc acccagaaga ctgtgga                                        27

<210> SEQ ID NO 4
<211> LENGTH: 27
<212> TYPE: DNA
<213> ORGANISM: Artificial Sequence
<220> FEATURE:
<223> OTHER INFORMATION: anti-sense primer

<400> SEQUENCE: 4
tactccttgg aggccatgta ggccatg                                        27
```

PHARMACEUTICAL USES OF DITERPENE EXCAVATOLIDE B FROM A CORAL OR AN ANALOGUE THEREOF

BACKGROUND OF THE INVENTION

1. Field of the Invention

The invention relates to pharmaceutical use of diterpene compounds; particularly, to pharmaceutical use of a coral-produced diterpene, excavatolide B, from a coral or an analogue thereof.

2. Description of the Related Art

With the progression of civilization, we human beings not only have longevity, but also emphasize the quality of our daily lives. However, a specific and effective drug is still absent for many diseases nowadays, such as cancer, chronic pain and atherosclerosis.

Inflammation has been proven to play an important role in the occurrence of several diseases in many studies. The occurrence of the inflammation-related diseases is highly associated with chronic and long-term inflammation induced by free radicals, pollution, food, ages, and pressure.

Atherosclerosis leads to remold a blood vessel and further causes the reduction of the inside diameter of the vessel. Therefore, it is an important risk factor of one of the leading causes of death, acute and lethal cardiovascular diseases, such as myocardial infarction, stroke and peripheral vascular diseases (Libby, Am J Clin Nutr 83:456 S-460S, 2006). Atherosclerosis is proven to be a chronic inflammatory cardiovascular disease (Ross, N Engl J Med 340: 115-126, 1999). When intima cells of the blood vessel are pressed or injured, monocytes are induced to differentiate into macrophages and accumulate abundantly around the injured tissue. Through a series of inflammatory reactions, smooth muscle cells of the blood vessel proliferate and inflammatory cells accumulate, and such reactions damage the blood flow and lead to cardiovascular diseases finally (Lucas and Greaves, Exp Rev Mol Med 3:1-18, 2001; Gordon, Bioassays 17:977-986, 1995; Majno and Joris, Cells, Tissues and Disease: Principles of General Pathology, Blackwell Science, Cambridge, Mass., USA, 1996). In animal model studies, the inflammatory critical factors of inducible nitric oxide synthase and cyclooxygenase-2 are shown to play an important role in atherosclerosis (Cipollone, Lupus 14:756-759, 2005; Boyle, Curr Vasc Pharmacol 3:63-68, 2005). Furthermore, bulk of inducible nitric oxide synthase and cyclooxygenase-2 is expressed in the human atherosclerosis tissue that comprises macrophages and proliferated smooth muscle cells (Baker et al, Arterioscler Thromb Vasc Biol 19:646-655, 1999; Buttery et al, Lab Invest 75:77-85, 1996). Presently, inducible nitric oxide synthase and cyclooxygenase-2 inhibitors are proven to significantly prevent the occurrence of atherosclerosis (Burleigh et al, Circulation 105:1816-23, 2002; Hayashi et al, Atherosclerosis 187:316-324, 2006; Pratico et al, Arterioscler Thromb Vasc Biol 19:646-655, 2001).

According to the definition made by International Association for the Study of Pain (IASP), pain is an unpleasant sensory and emotional experience associated with actual or potential tissue damage, or described in terms of such damage. With the extension of longevity, the opportunities and duration of pain are raised. To estimate in the conservative way, the global anodyne consumption reaches around one hundred billion US dollars. Improving life quality through pain control is an important subject. Among various pains, the factors of neuropathic pain are diverse, such as reduced distal circulation due to diabetes mellitus, neuron damage due to amputation or injury, viral infection and unknown reasons. Clinically, anodynes are divided into addictive anodynes and non-addictive anodynes. The addictive anodyne mainly comprises opiate, but the effect thereof to neuropathic pain is not satisfactory. The non-addictive anodyne comprises a steroid type and a non-steroid type. The steroid anodyne relives pain mainly through an anti-inflammatory pathway. However, the steroid anodyne is nonspecific, and the side effects are significant. The long-term usage is prohibited. On the other hand, the non-steroid anodyne comprises a pain-relieving type (such as panadol) and an anti-inflammatory type (such as aspirin). A non-steroid anti-inflammatory drug (NSAID) is now known to be safe with fewer side effects. The mechanism of a specific NSAID is through inhibiting inducible nitric oxide synthase and cyclooxygenase-2 pathways to relieve pain (Turini and DuBois, Annual Rev Med 53:35, 2002; Handy et al, Br J Pharmacol 123:1119-1126, 1998; Osborne et al, Br J Pharmacol 126:1840-1846, 1999). The product of NO or PGE2 catalyzed by inducible nitric oxide synthase or cyclooxygenase-2 is shown to be critical to the occurrence, maintenance and sensitivity of pain in the central neural system and periphery tissues (Moalem and Tracey, Brain Res Rev 51:240-264, 2006). Compared to using nerve blockers for pain relieving, administering inducible nitric oxide synthase and cyclooxygenase-2 inhibitors does not affect movement and neuron. Therefore, it is an important aspect for drug development.

Skin is the largest organ in the body. As the primary interface between the body and environment, it serves as the first line of defense against microbial pathogens as well as physical and chemical stress or insults (Kupper T S, Fuhlbrigge R C. Nature reviews Immunology 2004, 4:211-222; Nestle F O, Di Meglio P, Qin J Z, Nickoloff B J. Nature reviews Immunology 2009, 9:679-691). The skin does not only serve as a physical and a chemical barrier, but is also an immune-competent organ that elicits effective innate and adaptive immune responses to protect the human body. The cutaneous immune system maintains a balance between restricting excessive inflammation following tissue damage or injury and preserving the ability to rapidly respond to pathogen infection (Jermy A. Nature Reviews Immunology 2010, 10:1). It is clear that inadequate or misdirected immune response is involved in the pathogenesis of a variety of acquired inflammatory skin disorders (Kupper T S, Fuhlbrigge R C. Nature reviews Immunology 2004, 4:211-222). Therefore, systematic investigation of the mechanisms of action of immunomodulatory agents on the skin's immune system is necessary for the development of therapies for skin disorders.

Acute inflammation is the initial immune response to harmful stimuli. Acute inflammation in the skin often involves an increase in the vascular permeability of skin tissues, resulting in an accumulation of fluid at the inflamed site (edema). The release of mediator molecules such as nitric oxide and prostaglandins also elicits vascular permeability, thus permitting the efficient migration of leukocytes, mainly neutrophils, to the inflamed tissue site. Matrix metalloproteinase-9 (MMP-9) has been reported to be a crucial player in such neutrophil migration by degrading some major cellular components of the epidermis and dermis (Nagaoka I, Hirota S. Inflamm Res 2000, 49:55-62). In addition, it is well-known that secretions of cytokines such as TNF-α, IL-1α and IL-6 by keratinocytes or antigen-specific cells can play a key role in mediating the cutaneous inflammatory response (Nestle F O, Di Meglio P, Qin J Z, Nickoloff B J. Nature reviews Immunology 2009, 9:679-691; De Vry C G, Valdez M, Lazarov M, Muhr E, Buelow R, Fong T, Iyer S. J Invest Dermatol 2005, 125:473-481; Cumberbatch M, Dearman R J, Kimber I Immunology 1996, 87:513-518). These mediators were employed as indicators of skin inflammation in this study.

Several novel approaches have been explored to manage risk factors for skin cancers, tissue damage from UVB exposure, and inflammatory skin disorders (Staniforth V, Huang W C, Aravindaram K, Yang N S. The Journal of Nutritional Biochemistry, In Press). Several phytochemicals and tissue extracts from medicinal plants have been reported to confer immunostimulatory activities and have potential clinical applications (Nair H B, Sung B, Yadav V R, Kannappan R, Chaturvedi M M, Aggarwal B B. Biochem Pharmacol 2010, 80:1833-1843; Wang C Y, Staniforth V, Chiao M T, Hou C C, Wu H M, Yeh K C, Chen C H, Hwang P I, Wen T N, Shyur L F, Yang N S. BMC Genomics 2008, 9:479). A small phytochemical from *Lithospermum erythrorhizon* (shikonin) is previously reported to be able to inhibit the transcriptional activation of human TNF-α promoter in vivo in mouse skin (Staniforth V, Wang S Y, Shyur L F, Yang N S. J Biol Chem 2004, 279:5877-5885).

Caffeic acid is also shown to suppress UVB radiation-induced expression of IL-10 and activation of MAPKs in mouse skin tissues (Staniforth V, Chiu L T, Yang N S. Carcinogenesis 2006, 27:1803-1811). More recently, ferulic acid, a phenolic phytochemical, is demonstrated to be able to effectively inhibit UVB-induced matrix metalloproteinases in mouse skin via a posttranslational mechanism (Staniforth V, Huang W C, Aravindaram K, Yang N S. The Journal of Nutritional Biochemistry, 2012, 23:443-451).

Natural products from plants and terrestrial microorganisms have traditionally provided good sources of lead compounds/agents for human medicines. However, due to the biological diversity of the marine environment and the discovery of marine compounds with certain unique structures and pharmacological activities, compounds from marine organisms are expected to be a major source of lead compounds for future generations of pharmaceuticals (Marris E. Nature 2006, 443:904-905). A spectrum of different novel marine compounds have been identified, and their bioactivities evaluated for potential pharmaceutical application (Blunt J W, Copp B R, Munro M H, Northcote P T, Prinsep M R. Nat Prod Rep 2005, 22:15-61). Marine organisms are a possible extracting source of pharmaceutical compounds.

SUMMARY OF THE INVENTION

The invention provides a briarane-type diterpene, excavatolide B, or an acyloxyl analogue and pharmaceutical use thereof. The compounds are shown to be able to treat a disease associated with inducible nitric oxide synthase, cyclooxygenase-2, and/or matrix metalloproteinase-9.

According to the invention, the diterpene compound, excavatolide B (BrD1), is represented by the following Formula 1, Formula 1

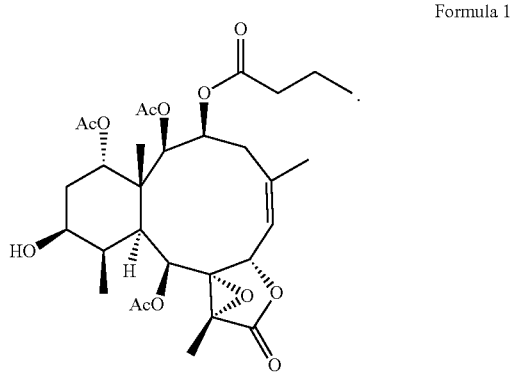 [SMILES: CCCC(=O)O[C@H]1C/C(C)=C\[C@@H]2OC(=O)[C@]3(C)O[C@]23[C@@H](OC(C)=O)[C@H]2[C@@H](C)[C@@H](O)C[C@H](OC(C)=O)[C@]2(C)[C@H]1OC(C)=O]

The invention also provides a method for treating a disease associated with TNF and/or IL-6 over-expression comprising administering a subject with said compound represented by Formula 1 or the acyloxyl analogue thereof.

DETAILED DESCRIPTION OF THE INVENTION

Figure 1A:
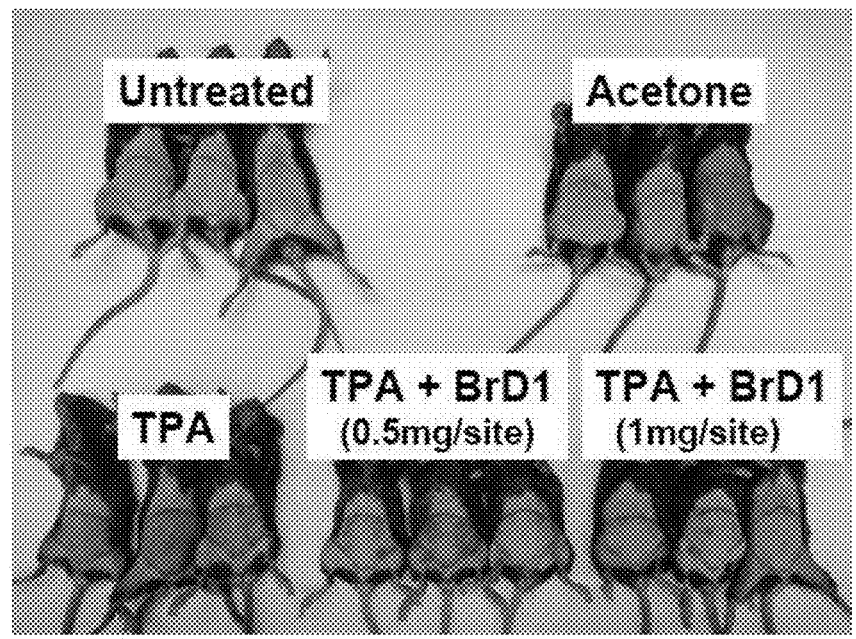
FIG. 1. Briarane-type diterpene, excavatolide B (BrD1), inhibits TPA-induced vascular permeability in mouse skin. Abdominal skins of female C57BL/6 mice were treated topically with TPA (10 nmol) or acetone (vehicle control) for 6 h, or treated with TPA for 10 min and then treated for 6 h with the indicated concentrations of BrD1. One percent Evans blue dye (100 µl) was injected into mouse tail veins for 20 min. (A) Photograph of mouse abdominal skins subjected to various treatments and vascular permeability test. (B) Photographs of the dermal (internal) sides of representative abdominal skins subjected to the above treatment and test. (C) Evans blue extravasation in test skins was determined by assay of optical density at 620 nm. *, P<0.05, and **, P<0.01 versus LPS control. Data are representative of two independent experiments.

The diterpene compound, excavatolide B, which is isolated from *Briareum excavatum*, or an acyloxyl analogue thereof is shown to inhibit the activity of inducible nitric oxide synthase, cyclooxygenase-2, and/or matrix metalloproteinase-9. Therefore, excavatolide B or the analogue thereof is able to treat a disease associated with inducible nitric oxide synthase, cyclooxygenase-2, and/or matrix metalloproteinase-9.

According to the invention, the diterpene compound, excavatolide B, is represented by the following Formula 1,

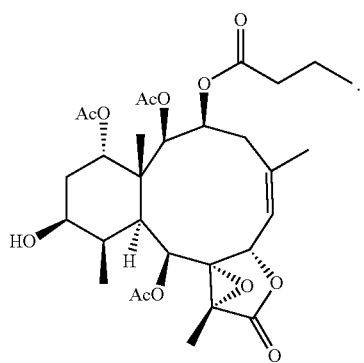

Formula 1

The diterpene compound, excavatolide B, represented by Formula 1 according to the invention can be obtained from a nature source, or can be also obtained by a chemical synthesis. Preferably, the compound is obtained from the nature source. Example of an extract process is shown by Sheu J H, Sung P J, Cheng MC, Liu H Y, Fang L S, Duh C Y, Chiang M Y. J Nat Prod 1998, 61:602-608 and Sheu J H, Sung P J, Su J H, Wang G H, Duh C Y, Shen Y C, Chiang M Y, Chen I T. J Nat Prod 1999, 62:1415-1420. Such documents are incorporated herein as references.

The acyloxyl analogue according to the invention comprises an acyloxyl group. The location of the acyloxyl group is a chemically acceptable one. In one preferred embodiment of the invention, the analogue of the compound represented by Formula 1 comprises an acyloxyl group for substituting a hydroxyl group in the C-12 position.

The acyloxyl group according to the invention is substituted or unsubstituted; preferably unsubstituted. In another aspect, the number of carbon atom of the acyloxyl group is not limited, and preferably is 2 to 12; more preferably is 4 to 10. In still another aspect, the acyloxyl group is straight or branched; preferably straight.

In one preferred embodiments of the invention, the acyloxyl analogue of the compound represented by Formula 1 is represented by one of the following formulae 2 to 5,

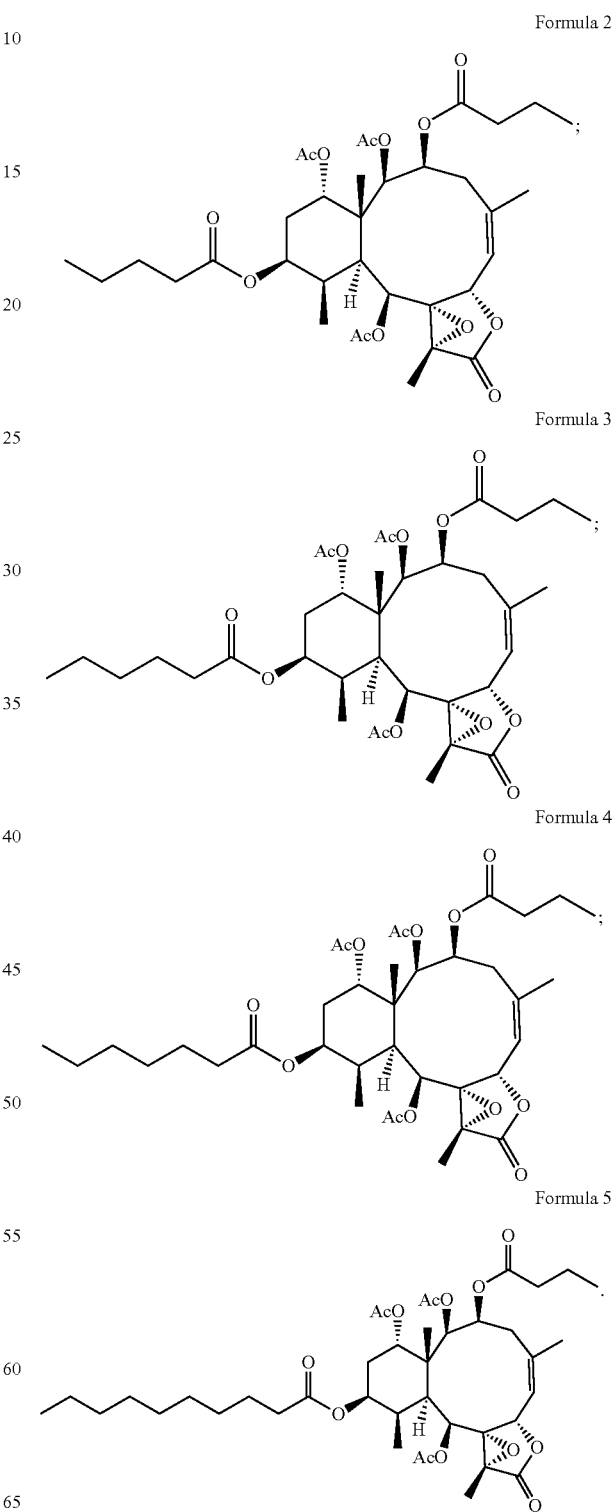

The preparation of the acyloxyl analogue can be a process of synthesizing an acyloxyl analogue of a diterpene compound. In one preferred embodiment of the invention, an appropriate acyl chloride (0.02 mmol) is added to a solution of excavatolide B (10 mg) in 5 ml of pyridine; the mixture is allowed to stand overnight at room temperature. Four milliliters of water is added to the reaction mixture followed by extraction with EtOAc (5 ml×3). The EtOAc layers are combined, dried over anhydrous $MgSO_4$ and evaporated. The afforded residue is purified by column chromatography on silica gel using EtOAc/hexane (1:8) as eluent to yield analogues represented by Formulae 2 to 5. Yields varies from 61.6% to 78.3%.

The present invention also provides a method for inhibiting inducible nitric oxide synthase, cyclooxygenase-2, and/or matrix metalloproteinase-9 comprising administering a subject with the compound represented by Formula 1 or an acyloxyl analogue thereof. Preferably, the present invention provides a method for inhibiting inducible nitric oxide synthase, cyclooxygenase-2, and/or matrix metalloproteinase-9 comprising administering a subject with the compound represented by Formula 1 or an acyloxyl analogue thereof.

Because the compound represented by Formula 1 or an acyloxyl analogue thereof has ability to inhibit the accumulation of inducible nitric oxide synthase, cyclooxygenase-2, and/or matrix metalloproteinase-9, it is useful in treating a disease associated with inducible nitric oxide synthase, cyclooxygenase-2, and/or matrix metalloproteinase-9. Preferably, because the compound represented by Formula 1 or the acyloxyl analogue thereof has ability to inhibit the accumulation of inducible nitric oxide synthase, cyclooxygenase-2, and/or matrix metalloproteinase-9, simultaneously, it is useful in treating a disease associated with inducible nitric oxide synthase, cyclooxygenase-2 and matrix metalloproteinase-9.

Figure 3A:
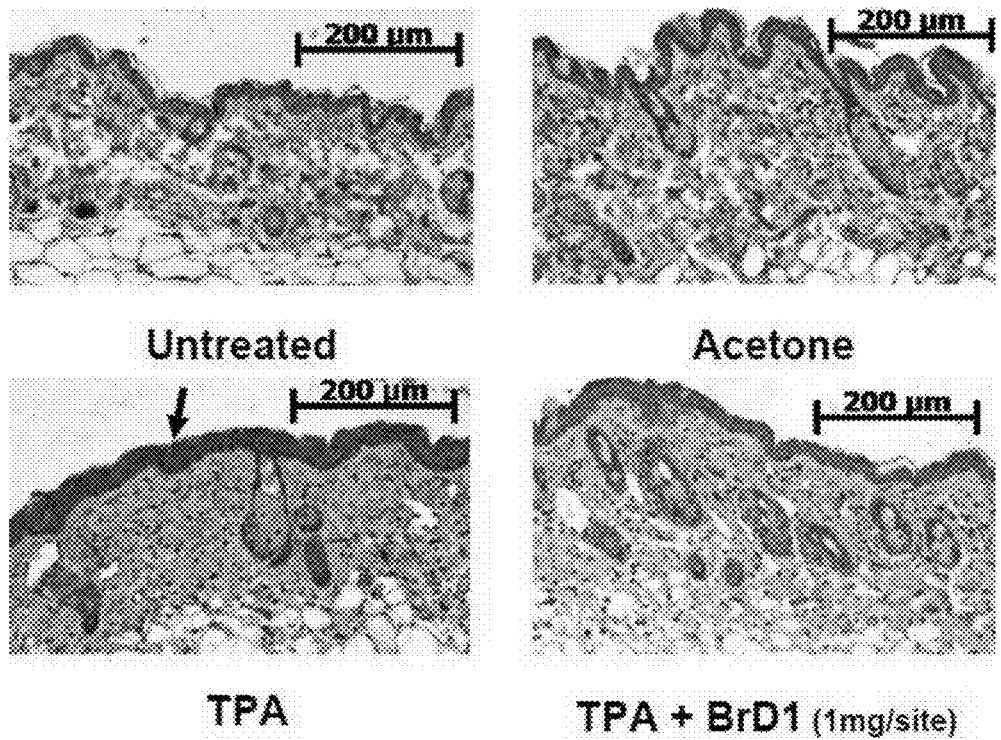
FIG. 3. BrD1 suppresses TPA-induced iNOS expression in mouse skin. Abdominal skins of female C57BL/6 mice were topically treated as described in FIG. 1. Longitudinal tissue sections of abdominal skins were immunostained for COX-2 (A) and iNOS (B) proteins and counter-stained with hematoxylin, as described in Examples. Positive staining for COX-2 and iNOS are visualized as brownish cells in the dermis and epidermis (arrow). Data are representative of two independent experiments.
Figure 3B:
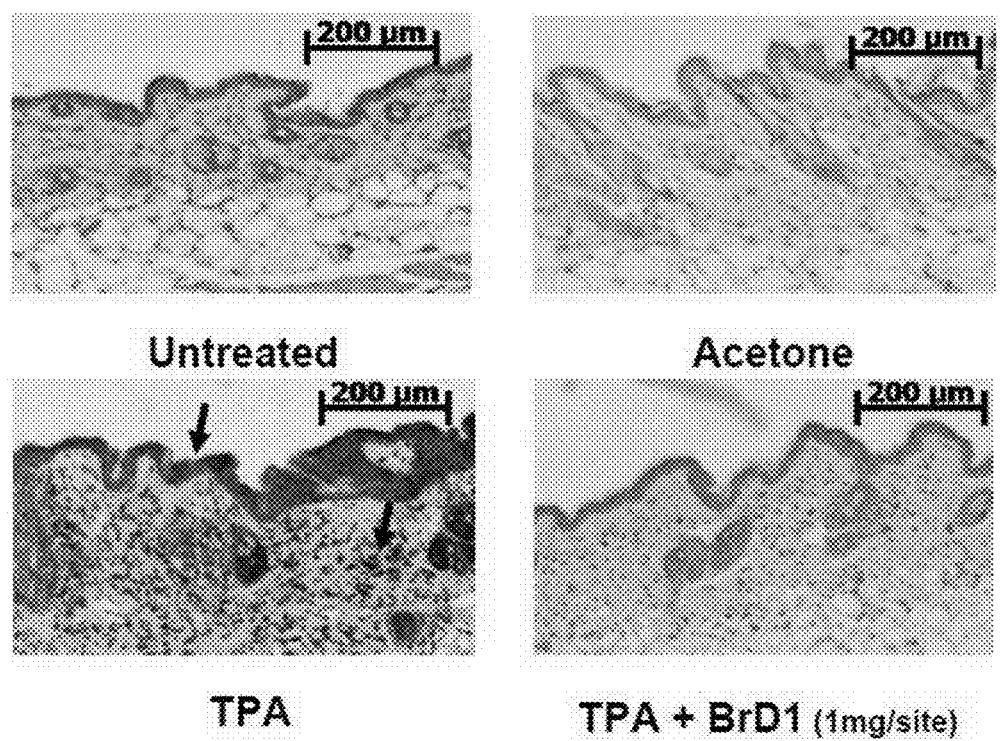

In one preferred embodiment of the invention, abdomens of female C57BL/6 mice are treated topically with TPA (12-O-tetradecanoyl-13-phorbol-acetate, 10 nmol) or acetone (vehicle control) for 6 h, or treated first with TPA for 10 min and then with the indicated concentrations of excavatolide B according to the invention for 6 h, and then stained it immunohistochemically with anti-COX-2 and anti-iNOS antibodies. As seen in FIGS. 3A and 3B, TPA treatment stimulates COX-2 expression in the epidermal layer, and TPA treatment strongly stimulates iNOS production in the epidermal and dermal layers as compared with those of the untreated or vehicle control-treated mice. Furthermore, excavatolide B according to the invention treatment reduces the TPA-induced COX-2 expression in the epidermis (FIG. 3A) and markedly reduces the TPA-induced iNOS expression in the epidermal and dermal layers of test mouse skin (FIG. 3B).

Many diseases have been reported to be related to the function of inducible nitric oxide synthase and/or cyclooxygenase-2, such as arthritis (Cuzzocrea et al, Arthritis Rheum. 52:1929-40, 2005), multiple sclerosis (Misko et al, J. Neuroimmunol. 61:195-204, 1995), inflammatory pain (Toriyabe et al, Anesthesiology 101, 983-990, 2004), and spinal cord injury (Lopez-Vales et al, Spine. 31:1100-6, 2006). Therefore, the disease is preferably selected from the group consisting of inflammation, atherosclerosis, neuropathic pain, inflammatory neointimal proliferation, arthritis, multiple sclerosis, inflammatory pain, and spinal cord injury.

Figure 4A:
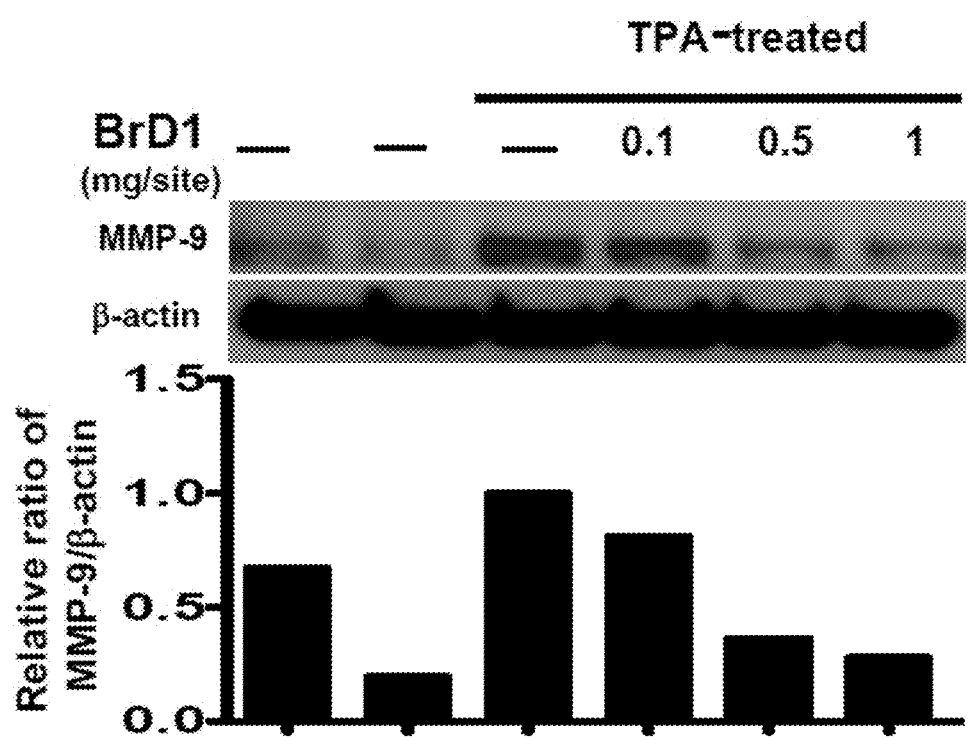
FIG. 4. BrD1 inhibits TPA-induced MMP-9 expression in mouse skin (A) Abdominal skins of female C57BL/6 mice were treated topically with TPA (10 nmol) or acetone (vehicle control) for 24 h, or treated with TPA for 10 min and then treated for 24 h with indicated concentrations of BrD1. Skin samples were collected, processed and analyzed for MMP-9 protein expression using western blot analysis. Mouse β-actin was used as a control. (B) Abdominal skins of female C57BL/6 mice were topically treated as described in FIG. 1. MMP-9 mRNA expression was determined using RT-PCR assay. The ratio is presented as the value relative to the intensity of TPA-treated control skin. Data are representative of two independent experiments.
Figure 4B:
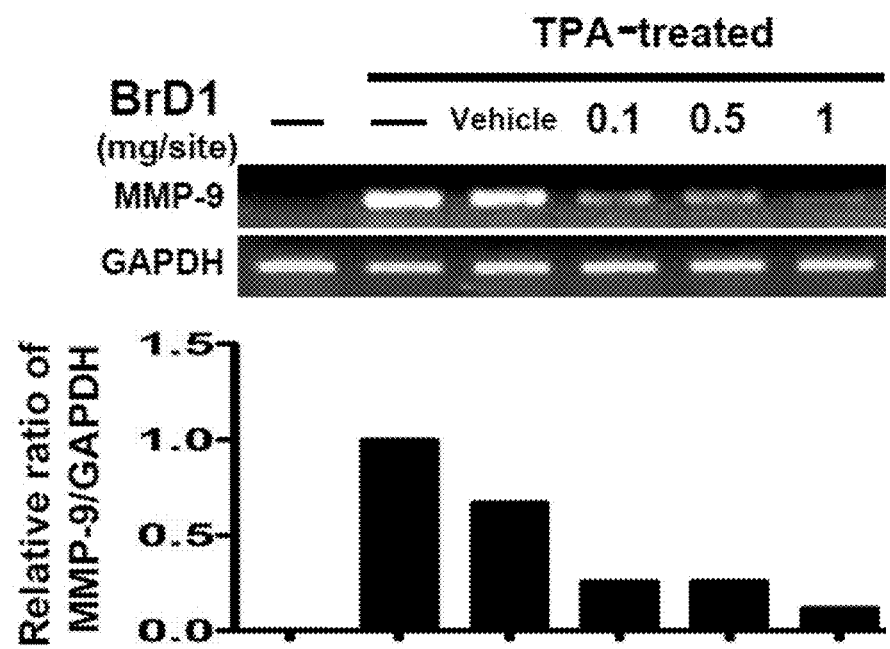

Matrix metalloproteinases (MMPs) play a crucial role in many physiological and pathological processes through remodeling extracellular matrix tissues (Stamenkovic I, J Pathol 2003, 200:448-464). Matrix metalloproteinase-9 (MMP-9), a gelatinase which has a key role in inflammatory response, is activated in skin during tissue injury (Shakarjian M P, Bhatt P, Gordon M K, Chang Y C, Casbohm S L, Rudge T L, Kiser R C, Sabourin C L, Casillas R P, Ohman-Strickland P, Riley D J, Gerecke D R. J Appl Toxicol 2006, 26:239-246). In order to evaluate the anti-inflammatory effect of excavatolide B according to the invention on MMP-9 activation in TPA-inflamed skin, excavatolide B according to the invention is topically applied after TPA treatment for 24 h. As seen in FIG. 4A, TPA treatment vigorously stimulates MMP-9 protein expression as compared with untreated or vehicle control groups. On the other hand, excavatolide B according to the invention significantly inhibits TPA-induced MMP-9 protein expression in a dose-dependent manner Inhibition with excavatolide B according to the invention treatment (1 mg/site/mouse) is up to a maximum 89%. Inhibition of TPA-induced MMP-9 expression by excavatolide B according to the invention treatment can also be readily observed at the mRNA level. As shown in FIG. 4B, TPA strongly stimulates MMP-9 mRNA expression and excavatolide B according to the invention applied topically after TPA treatment also significantly inhibits MMP-9 mRNA expression in a dose-dependent manner Excavatolide B according to the invention treatment (1 mg/site/mouse) inhibits MMP-9 mRNA expression up to a maximum 82%.

In one preferred embodiment of the invention, the inhibition of inducible nitric oxide synthase, cyclooxygenase-2, and/or matrix metalloproteinases is associated with Akt/NF-κB signal transduction pathway. The immuno-associated transcription factor NF-κB is a key upstream mediator of iNOS and MMP-9 expressions, and is known to be involved in various cutaneous inflammatory responses. Therefore, the invention provides a method for treating a disease associated with Akt/NF-κB signal transduction pathway.

Figure 5A:
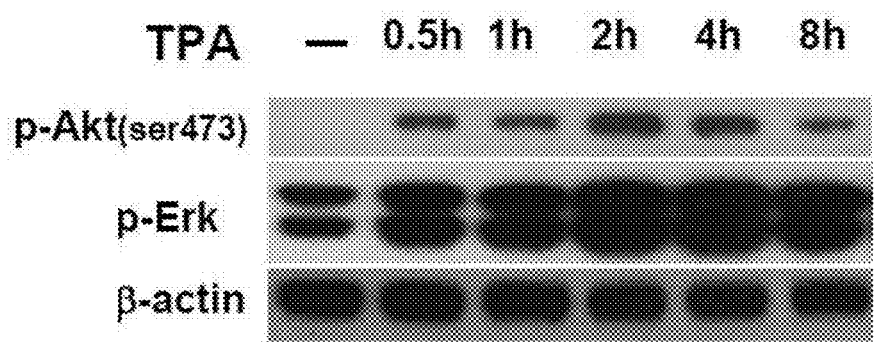
FIG. 5. BrD1 inhibits TPA-induced NF-kB and Akt activation in mouse skin. (A) Mouse skin was untreated or TPA-treated for indicated time points, and test skin samples were collected and analyzed for phosphorylation levels of Akt and Erk1/2. (B) Abdominal skins of female C57BL/6 mice were treated topically with TPA (10 nmol) or acetone for 2 h or treated with TPA for 10 min and then treated for 2 h with the indicated concentrations of BrD1 for 2 h. Skin samples were collected, processed and analyzed for the phosphorylation levels of Akt, NF-κB, IκBα and Erk1/2 by Western blot analysis. Mouse β-actin was used as a control. The ratio is presented as the value relative to the intensity of TPA-treated control skin Data are representative of two independent experiments.
Figure 5B:
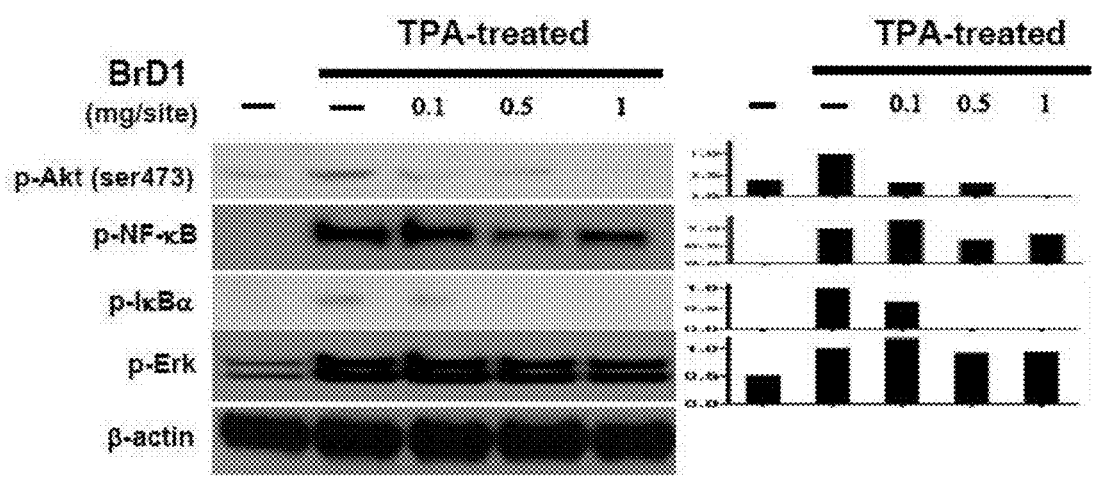

In one preferred embodiment of the invention, in order to assess the kinetics of Akt and Erk activation, abdominal skin is stimulated with TPA for 0.5 to 8h. A high level of phosphorylation of Akt and Erk is observed at 2 h after TPA treatment (FIG. 5A). TPA treatment strongly stimulates the phosphorylation of Akt, Erk, NF-κB and IκBα (FIG. 5B). Excavatolide B according to the invention seems to inhibit TPA-induced Erk phosphorylation only slightly. However, excavatolide B according to the invention treatment effectively inhibits the phoshporylation of NF-κB, and also significantly inhibits the TPA-stimulated phosphorylation of Akt and IκBα. These results indicate that excavatolide B according to the invention can significantly inhibit TPA-stimulated NF-κB and Akt activation in test mouse skin.

In one preferred embodiment of the invention, the inflammatory is acute inflammatory. Acute inflammatory reactions are known to include changes in vascular permeability, edema and cellular infiltration (Rao T S, Currie J L, Shaffer A F, Isakson P C. Inflammation 1993, 17:723-741).

In another aspect, in one preferred embodiment of the invention, the inflammation is skin inflammation.

Figure 1B:
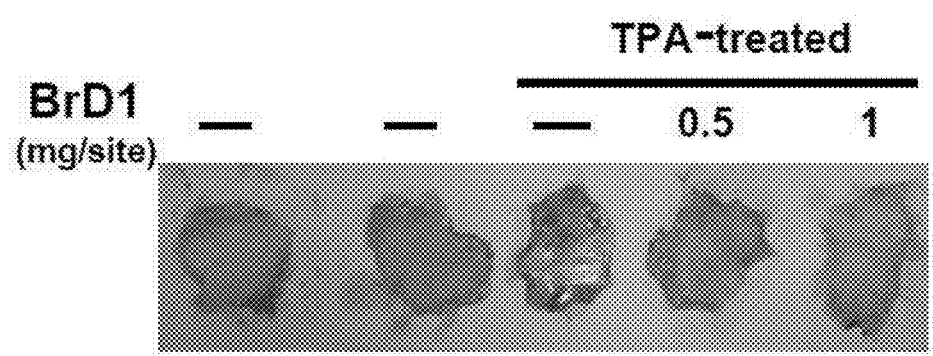
Figure 1C:
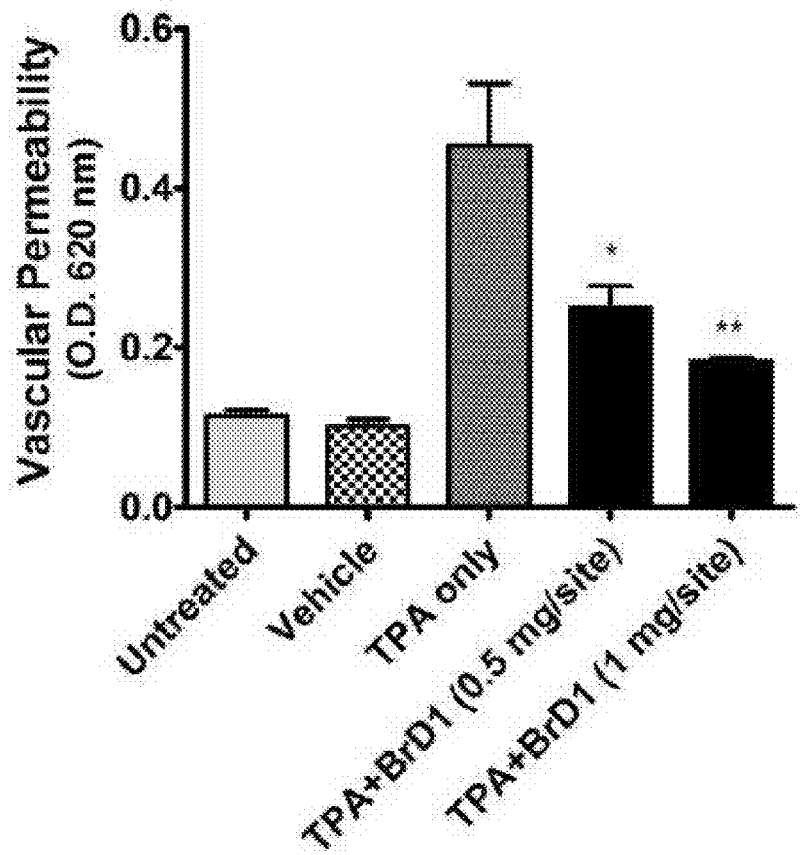
Figure 2A:
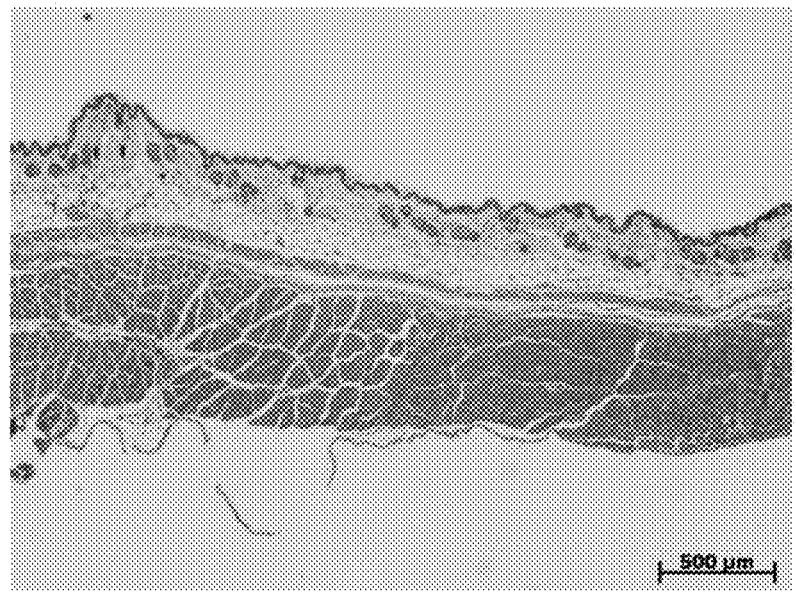
FIG. 2. BrD1 inhibits TPA-induced edema. Abdominal skins of female C57BL/6 mice were topically treated as described above in FIG. 1. Skin biopsies of abdominal skins were collected and stained with hematoxylin and eosin. a, b, c and d indicate the tissue layers: epidermis, dermis, hypodermis and peritoneum, respectively. Data are representative of two independent experiments. (A): untreated; (B): acetone (vehicle control); (C): TPA; (D): TPA+BrD1 (1 mg/site).
Figure 2B:
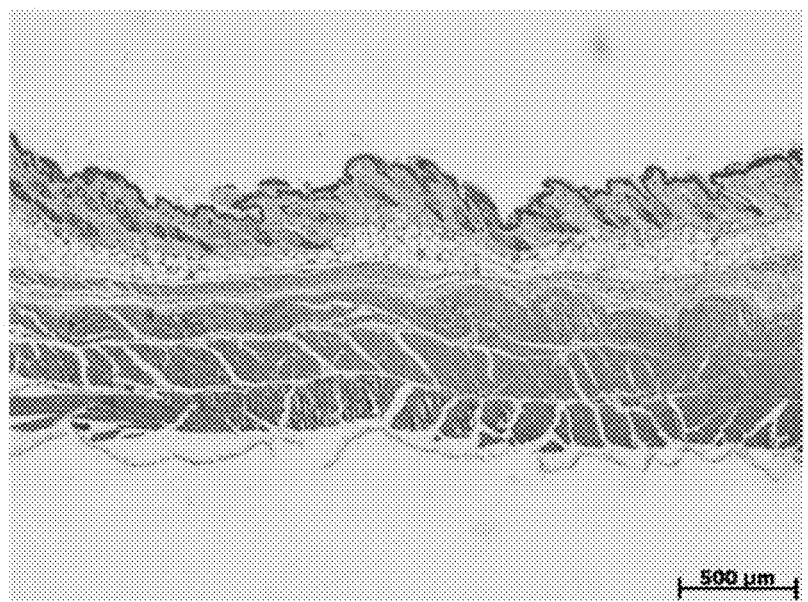
Figure 2C:
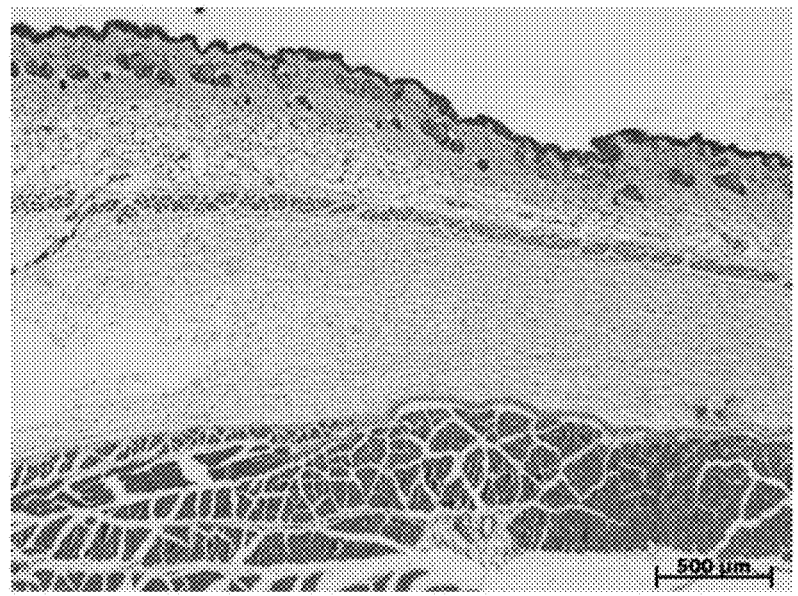
Figure 2D:
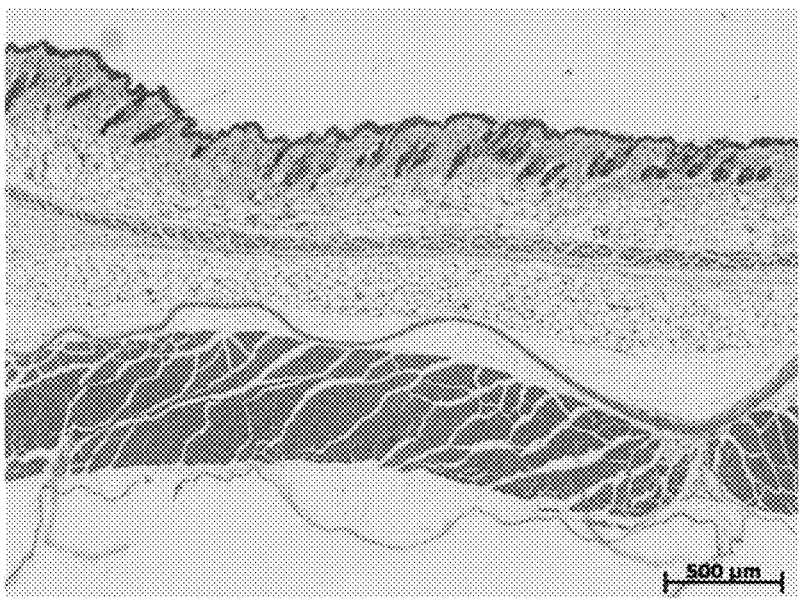

In one embodiment of the invention, abdomens of female C57BL/6 mice are treated topically with TPA (10 nmol) or acetone (vehicle control) for 6 h, or treated first with TPA for 10 min and then with the indicated concentrations of excavatolide B according to the invention for 6 h. Mice are injected for 20 min via the tail vein with 100 µl of 1% Evans blue. TPA strongly increases vascular permeability (FIGS. 1A, 1B and 1C). Topical application of excavatolide B according to the invention after TPA treatment significantly inhibits the TPA-induced vascular permeability. The level of inhibition is approximately 58% (0.5 mg/site of excavatolide B according to the invention) and 77% (1 mg/site of excavatolide B according to the invention) (FIG. 1C). In another aspect, As seen in FIG. 2, topical application of TPA markedly increases the skin thickness, especially in the hypodermal layer as compared with that of untreated or vehicle control groups. Treatment with excavatolide B according to the invention after TPA application substantially decreases the skin thickness, indicating excavatolide B according to the invention can effectively inhibit TPA-induced edema in mouse abdominal skin.

The invention also provides a method for treating a disease associated with TNF and/or IL-6 over-expression comprising administering a subject with said compound represented by Formula 1 or an acyloxyl analogue thereof. In one preferred embodiment of the invention, the method is for mediating immunological reaction; more preferably, the method is for mediating dendritic cells. Several studies have reported that the secretion of specific cytokines, including IL-1β, TNF-α and IL-6 by keratinocytes and various immune cells is involved in cutaneous inflammation (Nestle F O, Di Meglio P, Qin J Z, Nickoloff B J. Nature reviews Immunology 2009, 9:679-691; De Vry C G, Valdez M, Lazarov M, Muhr E, Buelow R, Fong T, Iyer S. J Invest Dermatol 2005, 125:473-481; Cumberbatch M, Dearman R J, Kimber I. Immunology 1996, 87:513-518).

In one embodiment of the invention, excavatolide B according to the invention is effective on inhibiting the LPS-induced expressions of TNF-α and IL-6 in mouse bone marrow-derived dendritic cells.

Figure 6A:
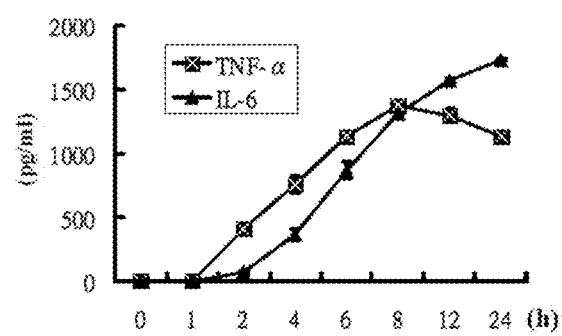
FIG. 6. BrD1 inhibits LPS-induced IL-6 and TNF-α expression in mouse BMDCs. (A) BMDCs from C57BL/6 mice were treated with LPS (100 ng/ml) for 1 to 24 h. (B) BMDCs from C57BL/6 mice were treated with LPS (100 ng/ml) for 24 h or LPS plus BrD1 at different concentrations for 24 h. Levels of IL-6 and TNF-α proteins in supernatants of conditioned media were analyzed by ELISA. *, P<0.05, and ***, P<0.001 versus LPS control. Data are representative of two independent experiments.
Figure 6B:
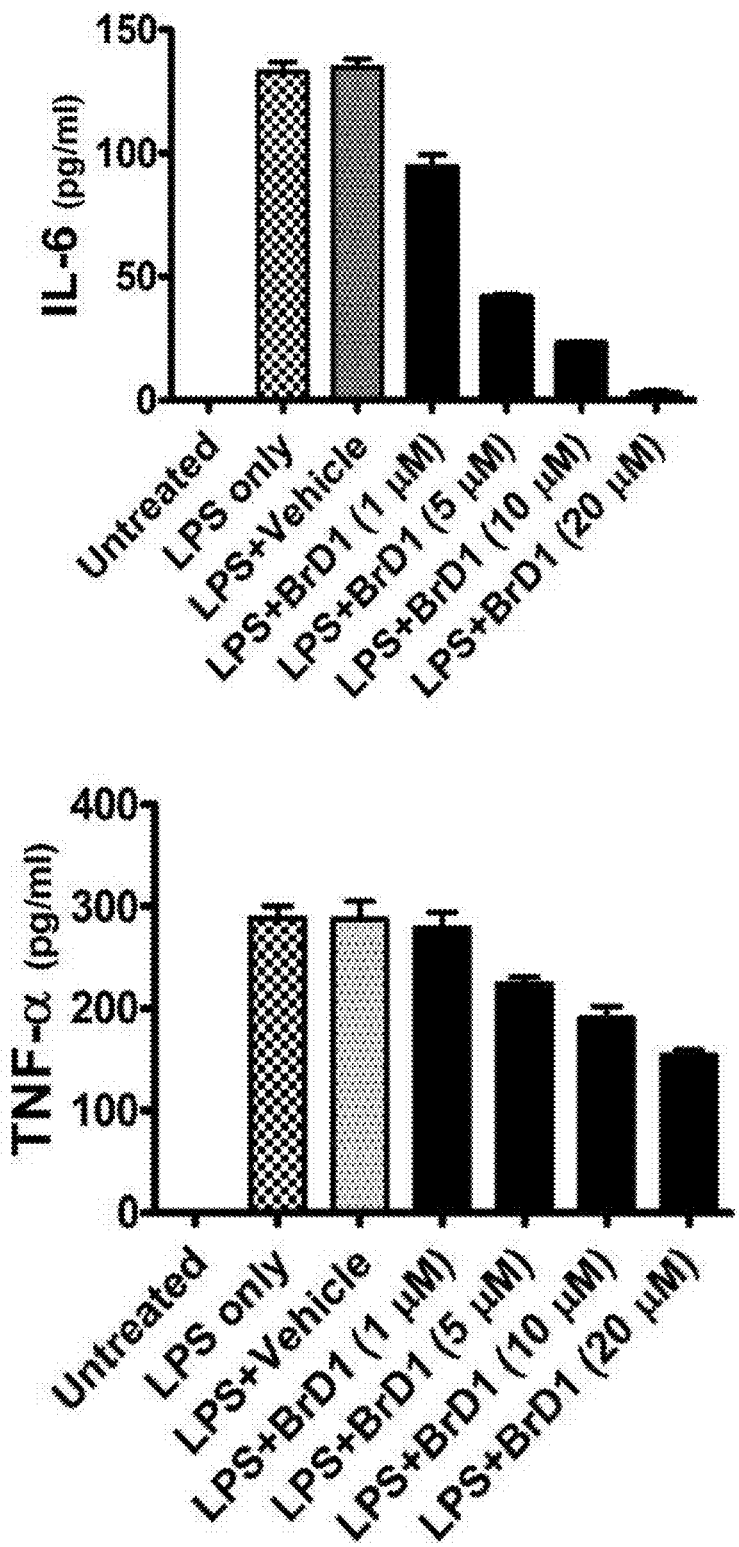

In one embodiment of the invention, after LPS stimulation, a high expression of TNF-α and IL-6 is maintained at 24 h (FIG. 6A). Excavatolide B according to the invention treatment strongly inhibits IL-6 expression in LPS-stimulated dendritic cells, and inhibits TNF-α expression to a much lesser extent (FIG. 6B).

The compound according to the invention can be administered orally or through injection. Preferably, the compound is administered by injection.

The following examples are given for the purpose of illustration only and are not intended to limit the scope of the present invention.

Example

Methods

Reagents

Recombinant cytokines mIL-4 and mGM-CSF were purchased from PeproTech (Rocky Hill, N.J.) mmTPA (12-O-tetradecanoyl-13-phorbol-acetate), Evans blue dye, N,N-dimethyl-formamide and LPS (*Escherichia coli* 055:B5) were purchased from Sigma-Aldrich (St. Louis, Mo.). The diterpene compound acyloxyl analogues thereof were prepared from excavatolide B as previously described.

Mice

Female C57BL/6JNarl mice (5-6 weeks old) were purchased from the National Laboratory Animal Breeding and Research Center, Taipei, Taiwan. All mice were maintained in a laminar airflow cabinet in a specific pathogen free (SPF) animal room kept at 24±2° C. and 40-70% humidity with a 12 h light/dark cycle under SPF conditions. All facilities were approved by the Institutional Animal Care and Utilization Committee of Academia Sinica, and animal experiments were all conducted according to institutional guidelines.

Preparation of 12-Acyloxyl Analogues of BrD1

An appropriate acyl chloride (0.02 mmol) was added to a solution of excavatolide B(BrD1, represented by Formula 1) (10 mg) in 5 ml of pyridine; the mixture was allowed to stand overnight at room temperature. Four milliliters of water was added to the reaction mixture followed by extraction with EtOAc (5 ml×3). The EtOAc layers were combined, dried over anhydrous MgSO4 and evaporated. The afforded residue was purified by column chromatography on silica gel using EtOAc/hexane (1:8) as eluent to yield analogues of BrD1 represented by Formulae 2 to 5 (BrD1-5C, BrD1-6C, BrD1-7C and BrD1-10C). Yields varied from 61.6% to 78.3%.

Measurement of Vascular Permeability

TPA-induced vascular permeability assay was modified and performed as previously described (Thurston G, Suri C, Smith K, McClain J, Sato T N, Yancopoulos G D, McDonald D M. Science 1999, 286:2511-2514). Shaved abdominal skins of female C57BL/6JNarl mice were topically treated with vehicle (acetone, 200 μl/site) or TPA (10 nmol in 200 μl acetone/site) for 6 h or treated with TPA for 10 min and subsequently treated for 6 h with the indicated concentrations of BrD1. Abdominal skins of untreated mice were used as the control group. One percent Evans blue dye (100 μl) was injected into mouse tail veins. After 20 min, anatomical appearances of mouse abdomens from the various treatments were photographically recorded. Abdominal skins representative of each test group were removed, turned over and photographed. Evans blue dye extravasated into the skins was extracted by incubation of the skin samples in 99% N,N-dimethyl-formamide overnight at 60° C. and optical density was measured at 620 nm.

Generation of Mouse Bone Marrow-Derived Dendritic Cells

For mouse bone marrow-derived DCs (BMDCs), five to six-week-old female C57BL/6JNarl mice were purchased from the National Laboratory Animal Center, Taiwan and kept under SPF conditions. BMDCs were generated from bone marrow cells of C57BL/6 mice as described previously (Yin S Y, Wang W H, Wang B X, Aravindaram K, Hwang P I, Wu H M, Yang N S. BMC genomics 2010, 11:612). In brief, bone marrow was isolated from femurs and tibiae which were then flushed with RPMI-1640 medium using a syringe with a 0.45-mm needle on Day 0. Red blood cells in suspension were lysed for 5 mM with ACK lysing buffer (150 mM NH4Cl, 1.0 mM KHCO3, 0.1 mM EDTA). Bone marrow cells were suspended at a density of $1\times10^7$ cells/30 ml in RPMI-1640 containing 10% FBS, 2 mM L-glutamine, 1% of nonessential amino acids, 100 U/mL penicillin and 100 μg/mL streptomycin supplemented with 20 ng/mL of mGM-CSF in 15-cm dishes at 37° C. with 5% CO2. On day 2, two-thirds of the medium was removed and 30 mL fresh medium with mGM-CSF was added to the cells. On day 5, culture plates were gently swirled and the floating and loosely adherent cells were discarded. Aliquots of 75% culture media were replenished with 20 ng/mL mGM-CSF and 20 ng/mL mIL-4. On day 7, mouse BMDCs (95% pure CD11b and MHC II) were harvested and incubated in RPMI 1640 medium containing 1 mM sodium pyruvate, 0.1 mM nonessential amino acids, 100 U/ml penicillin, 100 μg/ml streptomycin, and supplemented with 10% fetal bovine serum (Invitrogen, Carlsbad, Calif.) for 24 h at 37° C. with or without test chemicals in the presence or absence of LPS (100 ng/ml).

Measurement of Pro-Inflammatory Cytokines

BMDCs were treated with or without test chemicals in the presence or absence of LPS (100 ng/ml) for 24 h at 37° C. Aliquots of supernatants from DC cultures were assayed for IL-6 and TNF-α using commercial ELISA kits (R&D Systems, Minneapolis, Minn.) following the manufacturer's recommendations.

Primer Design and RT-PCR

Shaven abdominal skins of female C57BL/6JNarl mice were untreated or topically treated with vehicle (acetone, 200 ml/site) or TPA (10 nmol in 200 ml acetone/site) for 6 h or treated first with TPA for 10 min and then with the indicated concentrations of BrD1 for 6 h. Total RNA was extracted from treated abdominal skins of female mice using TRIzol reagent (Invitrogen Corp., Carlsbad, Calif.). RT-PCR reactions using AccessQuick RT-PCR system (Promega, Madison, Wis.) were carried out as described previously. The primers contained the following sequences: mouse MMP-9 sense primer 5'-CTAGTGAGAGACTCTACACGGAG-3' (SEQ ID NO. 1), and anti-sense primer 5'-GAGCCACGACCATACA-GATACTG-3' (SEQ ID NO. 2); mouse GAPDH sense primer 5'-CATCACTGCCACCCAGAAGACTGTGGA-3' (SEQ ID NO. 3), and anti-sense primer 5'-TACTCCTTGGAGGC-CATGTAGGCCATG-3' (SEQ ID NO. 4). Gel images were scanned and densitometry analysis of the captured image was performed using Gene Tools software (Syngene, Cambridge, UK).

Histopathological Analysis

Mice were treated or not treated topically on their shaven abdomens with acetone (vehicle only) or TPA (10 nmol in 200 μl acetone/site) for 6 h or treated first with TPA for 10 min, then with the indicated concentrations of BrD1 for 6 h. Mice were killed by cervical dislocation. Abdominal skin tissues were collected, fixed with formalin buffer and embedded in paraffin. Tissue sections (5 mm) were cut and laid onto silanized glass slides and deparaffinized three times with xylene for 5 min each prior to rehydration using a graded alcohol bath. For hematoxyline and eosin staining, the sections were stained with hematoxyline and eosin staining. For immunohistochemical staining, the deparaffinized sections were boiled in 10 mM citrate buffer (pH 6.0) for 10 min for antigen retrieval and rinsed with PBS containing 0.05% Tween-20 buffer for 5 min. The sections were treated with 3% hydrogen peroxide in methanol for 15 min to decrease non-specific binding. They were subsequently washed with blocking solution (PBS containing 1% BSA) for 30 min and then PBST twice for 5 min. All slides were incubated first with 2% goat serum in blocking solution for 30 min, then with a 1:200 dilution of polyclonal iNOS antibody (eBioscience, San Diego, Calif.) at room temperature for 1 h. The slides were further developed using HPR EnVision™ system (Dako, Glostrup, Denmark). Subsequently, peroxidase-binding sites were determined by staining with 3,3'-diaminobenzidine tetrahydrochloride (Dako). Eventually, Mayer's hematoxyline was used for counterstaining Western Blotting Analysis Shaven abdominal skins of female C57BL/6JNarl mice were not treated or topically treated with vehicle (acetone, 200 μl/site) or TPA (10 nmol in 200 μl acetone/site) at indicated time points or treated first with TPA for 10 min, then with the indicated concentrations of BrD1 at the indicated time points. Abdominal skin samples were collected, homogenated and lysed to prepare total proteins. Protein samples were subsequently resolved by SDS-PAGE using a gradient gel. The resolved proteins were transferred to a PVDF Immobilon-P membrane (Millipore, Bedford, Calif.), and the membrane was blocked with 5% non-fat dry milk in PBST buffer (phosphate-buffered saline (PBS) containing 0.1% Tween 20) for 60 minutes at room temperature. The membranes were incubated overnight at 4° C. with commercially available antibodies (1:1000 dilutions). Loading of equal amounts of protein was assessed using mouse β-actin. The blots were rinsed three times with PBST buffer for 5 minutes. Washed blots were incubated with HRP-conjugated secondary antibody (1:100,000 dilution), then washed again three times with PBST buffer. The transferred proteins were visualized with an enhanced chemiluminescence (ECL) detection kit (Amersham Pharmacia Biotech, Buckinghamshire, UK). Quantification of bands was performed using Image J software.

Statistical Analysis

Statistical analyses were performed with GraphPad Prism software, version 5. Data are presented as mean±SD and statistical significance was determined by a one-way ANOVA followed by Tukey multiple comparison tests. Means were considered significantly different if the P value was less than 0.05.

Results

Excavatolide B (BrD1) effectively inhibits TPA-induced vascular permeability in mouse skin Acute inflammatory reactions are known to include changes in vascular permeability, edema and cellular infiltration (Rao T S, Currie J L, Shaffer A F, Isakson P C. Inflammation 1993, 17:723-741). In order to evaluate the anti-inflammatory effect of BrD1 on TPA-induced dermatitis in a murine model, we initially evaluated the possible inhibitory effect of BrD1 on TPA-induced vascular permeability. Abdomens of female C57BL/6 mice were treated topically with TPA (10 nmol) or acetone (vehicle control) for 6 h, or treated first with TPA for 10 min and then with the indicated concentrations of BrD1 for 6 h. Mice were injected for 20 min via the tail vein with 100 μl of 1% Evans blue. TPA strongly increased vascular permeability (FIGS. 1A, 1B and 1C). Topical application of BrD1 after TPA treatment significantly inhibited the TPA-induced vascular permeability. The level of inhibition was approximately 58% (0.5 mg/site of BrD1) and 77% (1 mg/site of BrD1) (FIG. 1C).

BrD1 Inhibits TPA-Induced Edema

Since increased vascular permeability is one of factors contributing to the formation of edema, we next evaluated whether BrD1 inhibited formation of edema in TPA-induced inflammation by examining H&E-stained longitudinal sections of skin samples. As seen in FIG. 2, topical application of TPA markedly increased the skin thickness, especially in the hypodermal layer as compared with that of untreated or vehicle control groups. Treatment with BrD1 after TPA application substantially decreased the skin thickness, indicating BrD1 can effectively inhibit TPA-induced edema in mouse abdominal skin.

BrD1 Suppresses TPA-Induced COX-2 and iNOS Expression in Mouse Skin

Cyclooxygenase-2 (COX-2) and inducible nitric oxide synthase (iNOS) are key mediators of various inflammation and immunity activities. A relatively high level of COX-2 and iNOS expression can be observed in skin during the acute phase of inflammation (Vane J R, Mitchell J A, Appleton I, Tomlinson A, Bishop-Bailey D, Croxtall J, Willoughby D A. Proc Natl Acad Sci USA 1994, 91:2046-2050). To examine whether BrD1 can also inhibit COX-2 and iNOS expression in TPA-inflamed skin, we applied BrD1 topically to TPA-treated skin for 6 h, and then stained it immunohistochemically with anti-COX-2 and anti-iNOS antibodies. As seen in FIGS. 3A and 3B, TPA treatment stimulated COX-2 expression in the epidermal layer, and TPA treatment strongly stimulated iNOS production in the epidermal and dermal layers as compared with those of the untreated or vehicle control-treated mice. Furthermore, BrD1 treatment reduced the TPA-induced COX-2 expression in the epidermis (FIG. 3A) and markedly reduced the TPA-induced iNOS expression in the epidermal and dermal layers of test mouse skin (FIG. 3B).

BrD1 Inhibits TPA-Induced MMP-9 Expression in Mouse Skin

Matrix metalloproteinases (MMPs) play a crucial role in many physiological and pathological processes through remodeling extracellular matrix tissues (Stamenkovic I. J Pathol 2003, 200:448-464). Matrix metalloproteinase-9 (MMP-9), a gelatinase which has a key role in inflammatory response, is activated in skin during tissue injury (Shakarjian M P, Bhatt P, Gordon M K, Chang Y C, Casbohm S L, Rudge T L, Kiser R C, Sabourin C L, Casillas R P, Ohman-Strickland P, Riley D J, Gerecke D R. J Appl Toxicol 2006, 26:239-246). In order to evaluate the anti-inflammatory effect of BrD1 on MMP-9 activation in TPA-inflamed skin, BrD1 was topically applied after TPA treatment for 24 h. As seen in FIG. 4A, TPA treatment vigorously stimulated MMP-9 protein expression as compared with untreated or vehicle control groups. On the other hand, BrD1 significantly inhibited TPA-induced MMP-9 protein expression in a dose-dependent manner Inhibition with BrD1 treatment (1 mg/site/mouse) was up to a maximum 89%. Inhibiton of TPA-inducedMMP-9 expression by BrD1 treatment could also be readily observed at the mRNA level. As shown in FIG. 4B, TPA strongly stimulated MMP-9 mRNA expression and BrD1 applied topically after TPA treatment also significantly inhibited MMP-9 mRNA expression in a dose-dependent manner BrD1 treatment (1 mg/site/mouse) inhibited MMP-9 mRNA expression up to a maximum 82%.

BrD1 Inhibits TPA-Stimulated NF-κB and Akt Activation in Mouse Skin

The roles of the Akt and Erk signaling pathways in inflammatory activities in mouse skin have been well-demonstrated. We therefore evaluated whether BrD1 could interfere with TPA-induced activation of Akt and Erk in inflamed skin. In order to assess the kinetics of Akt and Erk activation, abdominal skin was stimulated with TPA for 0.5 to 8 h. A high level of phosphorylation of Akt and Erk was observed at 2 h after TPA treatment (FIG. 5A). We therefore chose 2 h as the time point at which to assess the BrD1-associated signaling transduction activity in TPA-inflamed skin. The immuno-associated transcription factor NF-κB is a key upstream mediator of iNOS and MMP-9 expressions, and is known to be involved in various cutaneous inflammatory responses. We thus determined the phosphorylation level of Akt, Erk, NF-κB and IκBα in skins subjected to different treatments. TPA treatment strongly stimulated the phosphorylation of Akt, Erk, NF-θB and IxBa (FIG. 5B). BrD1 seemed to inhibit TPA-induced Erk phosphorylation only slightly. However, BrD1 treatment effectively inhibited the phoshporylation of NF-κB, and also significantly inhibited the TPA-stimulated phosphorylation of Akt and IκBα. These results indicate that BrD1 can significantly inhibit TPA-stimulated NF-κB and Akt activation in test mouse skin.

BrD1 Inhibits LPS-Induced IL-6 and TNF-α Expression in Mouse Bone Marrow-Derived Dendritic Cells Several studies have reported that the secretion of specific cytokines, including IL-1β, TNF-α and IL-6 by keratinocytes and various immune cells is involved in cutaneous inflammation (Nestle F O, Di Meglio P, Qin J Z, Nickoloff B J. Nature reviews Immunology 2009, 9:679-691; De Vry C G, Valdez M, Lazarov M, Muhr E, Buelow R, Fong T, Iyer S. J Invest Dermatol 2005, 125:473-481; Cumberbatch M, Dearman R J, Kimber I. Immunology 1996, 87:513-518). In order to investigate the anti-inflammatory effect of BrD1 on cytokine expression, mouse bone marrow-derived dendritic cells were used to evaluate the inhibitory effect of BrD1 on LPS-induced expressions of TNF-α and IL-6. In our time-course study for expression of TNF-α and IL-6, after LPS stimulation, a high expression of TNF-α and IL-6 was maintained at 24 h (FIG. 6A). We therefore chose 24 h as the time point at which to assess the expression of TNF-α and IL-6. BrD1 treatment strongly inhibited IL-6 expression in LPS-stimulated dendritic cells, and inhibited TNF-a expression to a much lesser extent (FIG. 6B).

Figure 7:
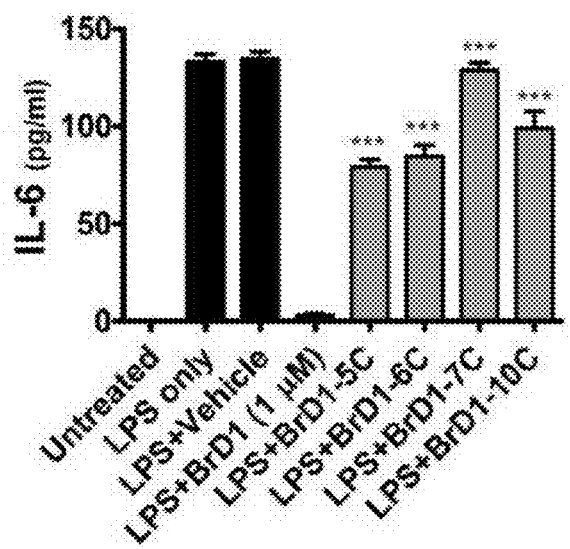
FIG. 7. Structure-activity relationship of briarane-type diterpenes that confer the inhibition of LPS-induced IL-6 expression in mouse BMDCs. The chemical structure of BrD1, and its analogs including BrD1-5C, BrD1-6C, BrD1-7C and BrD1-10C. Immature DCs were co-treated with LPS and BrDs at 20 μM. The level of IL-6 proteins in supernatants was determined using ELISA. ***, P<0.001 versus LPS+BrD1 treatment. Data are representative of two independent experiments.

Steric Hindrance of 12-Acyloxyl Substituents Reduces the Inhibitory Bioactivity of Briarane-Type Diterpenes Our results suggest that steric hindrance of the 12-acyloxyl substituents of BrDs decreases their inhibitory activity. In order to confirm this SAR, we semi-synthesized several analogues of BrD1 by replacing the hydroxyl group at C-12 with longer acyloxyl groups ($C_5$, $C_6$, $C_7$ and CO (FIG. 7). We then examined the inhibitory effect of BrD1 and these BrD1 analogues (BrD1-5C, BrD1-6C, BrD1-7C and BrD1-10C) on cytokine secretion activity in LPS-stimulated mature DCs. BrD1 significantly inhibited the expression of cytokine IL-6 in LPS-stimulated, mature DCs (FIG. 7). This inhibitory activity gradually decreased when the hydroxyl group at C-12 was replaced by longer acyloxyl groups ($C_5$ to $C_{10}$), confirming that steric hindrance of 12-acyloxyl substituents can effectively suppress the capacity of BrDs to inhibit LPS-induced IL-6 expression.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for treating a disease associated with inducible nitric oxide synthase, cyclooxygenase-2, and/or matrix metalloproteinase-9 comprising administering a subject with a compound represented by the following Formula 1 or an acyloxyl analogue thereof,

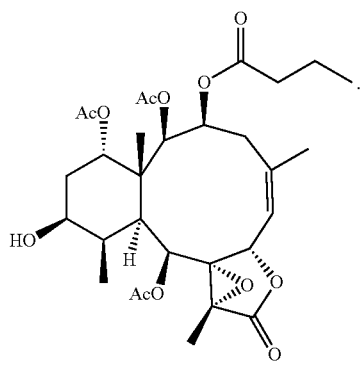

Formula 1

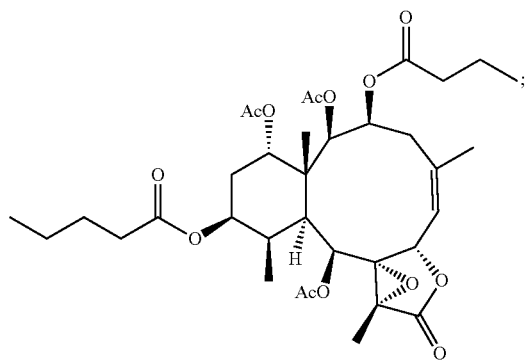

Formula 2

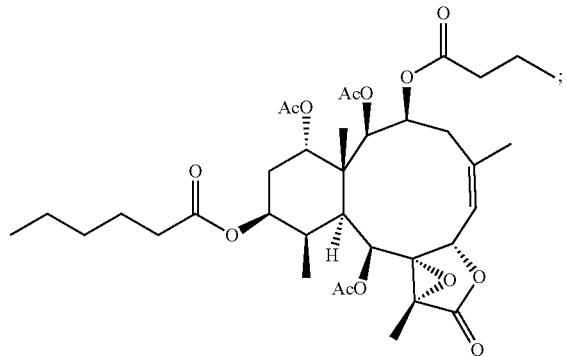

Formula 3

2. The method according to claim 1, wherein the acyloxyl analogue comprises an acyloxyl group for substituting a hydroxyl group in the C-12 position.

3. The method according to claim 1, wherein the acyloxyl analogue is selected from the group consisting of the compounds represented by the following formulae 2 to 5;

Formula 4

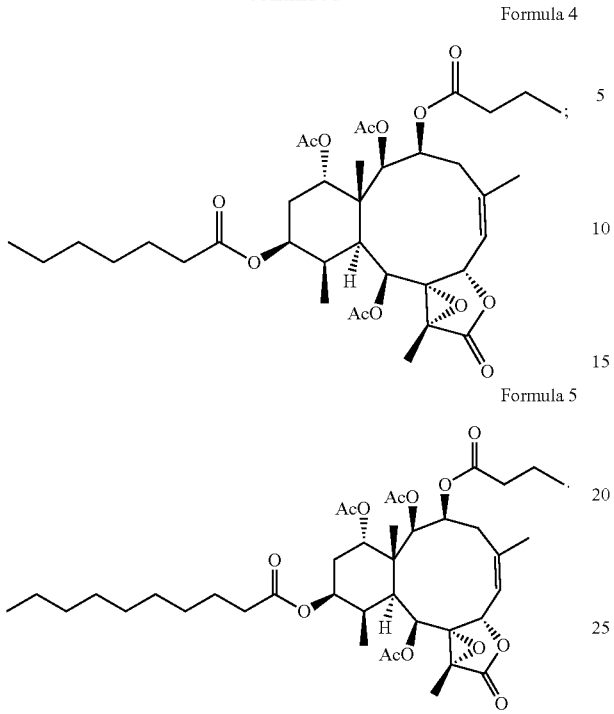

Formula 5

4. The method according to claim 1, wherein the disease is a disease associated with Akt/NF-κB signal transduction pathway.

5. The method according to claim 4, wherein the disease is selected from the group consisting of inflammation, atherosclerosis, neuropathic pain, inflammatory neointimal proliferation, arthritis, multiple sclerosis, inflammatory pain, and spinal cord injury.

6. The method according to claim 5, wherein the inflammation is acute inflammation.

7. The method according to claim 5, wherein the inflammation is skin inflammation.

8. The method according to claim 2, wherein the disease is a disease associated with Akt/NF-κB signal transduction pathway.

9. The method according to claim 8, wherein the disease is selected from the group consisting of inflammation, atherosclerosis, neuropathic pain, inflammatory neointimal proliferation, arthritis, multiple sclerosis, inflammatory pain, and spinal cord injury.

10. The method according to claim 9, wherein the inflammation is acute inflammation.

11. The method according to claim 9, wherein the inflammation is skin inflammation.

12. The method according to claim 1, wherein the compound represented by Formula 1 or the acyloxyl analogue thereof is administered by injection.

13. A method for treating a disease associated with TNF and/or IL-6 over-expression comprising administering a subject with a compound represented by the following Formula 1 or an acyloxyl analogue thereof, Formula 1

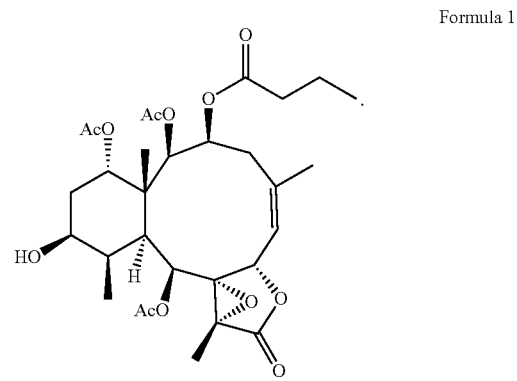 [SMILES: CCCC(=O)O[C@H]1C/C(C)=C\[C@@H]2OC(=O)[C@]3(C)O[C@]23[C@@H](OC(C)=O)[C@H]2[C@@H](C)[C@@H](O)C[C@H](OC(C)=O)[C@]2(C)[C@H]1OC(C)=O]

14. The method according to claim 13, wherein the acyloxyl analogue comprises an acyloxyl group for substituting a hydroxyl group in the C-12 position.

15. The method according to claim 13, wherein the acyloxyl analogue is selected from the group consisting of the compounds represented by the following formulae 2 to 5;

Formula 2

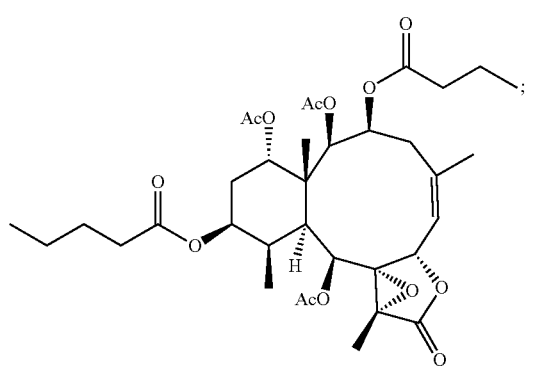

Formula 3

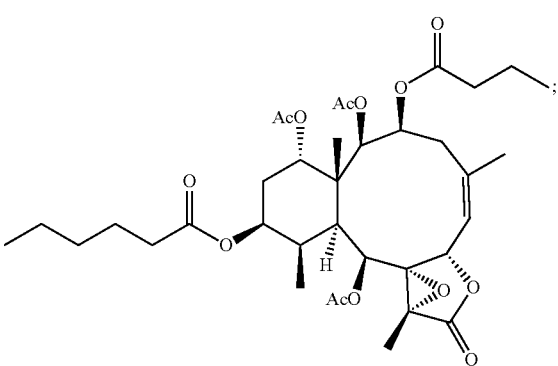

Formula 4

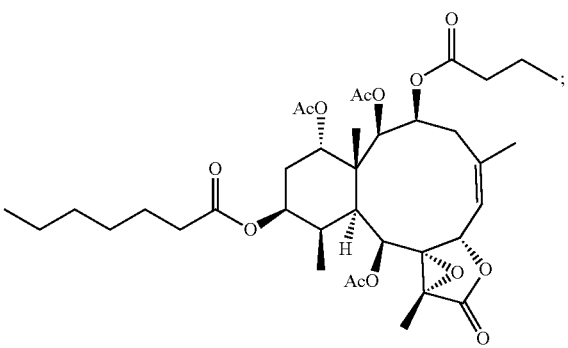

-continued

Formula 5

16. The method according to claim 13, which method is for mediating immunological reaction.

17. The method according to claim 16, which method is for mediating dendritic cells.

18. The method according to claim 14, which method is for mediating immunological reaction.

19. The method according to claim 18, which method is for mediating dendritic cells.

20. The method according to claim 13, wherein the compound represented by Formula 1 or the acyloxyl analogue thereof is administered by injection.

* * * * *